US011090238B2

(12) United States Patent
Rabe et al.

(10) Patent No.: US 11,090,238 B2
(45) Date of Patent: Aug. 17, 2021

(54) ARRAY OF COSMETIC COMPOSITIONS FOR CAMOUFLAGING TONAL IMPERFECTIONS

(71) Applicant: The Procter & Gamble Company, Cincinnati, OH (US)

(72) Inventors: Thomas Elliott Rabe, Baltimore, MD (US); Janette Villalobos Lingoes, Cincinnati, OH (US); Lissette D Schorsch, Cincinnati, OH (US); Tim Nolan, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/006,970

(22) Filed: Jun. 13, 2018

(65) Prior Publication Data

US 2018/0360709 A1    Dec. 20, 2018

Related U.S. Application Data

(60) Provisional application No. 62/520,764, filed on Jun. 16, 2017.

(51) Int. Cl.
| | |
|---|---|
| *A61K 8/27* | (2006.01) |
| *A61K 8/19* | (2006.01) |
| *A61K 8/29* | (2006.01) |
| *A61Q 1/02* | (2006.01) |
| *A45D 44/00* | (2006.01) |
| *A45D 40/24* | (2006.01) |
| *A61Q 1/08* | (2006.01) |
| *A45D 34/00* | (2006.01) |

(52) U.S. Cl.
CPC ............ *A61K 8/27* (2013.01); *A45D 40/24* (2013.01); *A45D 44/00* (2013.01); *A61K 8/19* (2013.01); *A61K 8/29* (2013.01); *A61Q 1/02* (2013.01); *A61Q 1/08* (2013.01); *A45D 2034/005* (2013.01); *A45D 2044/007* (2013.01); *A61K 2800/87* (2013.01)

(58) Field of Classification Search
CPC ... A61K 8/27; A61K 8/19; A61K 8/29; A61Q 1/02
See application file for complete search history.

(56) References Cited

U.S. PATENT DOCUMENTS

| | | | |
|---|---|---|---|
| 4,129,391 | A | 12/1978 | Gamacher |
| 4,270,526 | A | 6/1981 | Morales |
| 4,813,404 | A | 3/1989 | Vallis |
| 5,706,038 | A | 1/1998 | Jackson |
| 6,017,110 | A | 1/2000 | Jackson |
| 6,290,324 | B1 | 9/2001 | Jackson |
| 6,312,124 | B1 | 11/2001 | Desormeaux |
| 6,622,733 | B2 | 9/2003 | Saksa |
| 6,723,077 | B2 | 4/2004 | Pickup |
| 6,810,130 | B1 | 10/2004 | Aubert |
| 7,500,732 | B2 | 3/2009 | James |
| 7,544,190 | B2 | 6/2009 | Pickup |
| 7,648,364 | B2 | 1/2010 | Dauga |
| 7,798,599 | B2 | 9/2010 | Michael |
| 7,824,003 | B2 | 11/2010 | Studer |
| 7,890,152 | B2 | 2/2011 | Edgar |
| 8,007,062 | B2 | 8/2011 | Edgar |
| 8,027,505 | B2 | 9/2011 | Edgar |
| 8,231,292 | B2 | 7/2012 | Rabe |
| 8,695,610 | B2 | 4/2014 | Samain |
| 8,915,562 | B2 | 12/2014 | Edgar |
| 8,942,775 | B2 | 1/2015 | Edgar |
| 9,020,184 | B2 | 4/2015 | Edgar |
| 9,084,587 | B2 | 7/2015 | Eckhouse |
| 9,247,802 | B2 | 2/2016 | Edgar |
| 9,271,554 | B2 | 3/2016 | Nakashima |
| 9,449,382 | B2 | 9/2016 | Edgar |
| 9,462,872 | B2 | 10/2016 | Edgar |
| 9,522,101 | B2 | 12/2016 | Rabe |
| 9,592,666 | B2 | 3/2017 | Bush |
| 9,616,447 | B2 | 4/2017 | Bush |
| 9,616,668 | B1 | 4/2017 | Rabe |
| 9,616,692 | B1 | 4/2017 | Rabe |
| 9,650,525 | B1 | 5/2017 | Suthar |
| 9,757,947 | B2 | 9/2017 | Kuno |
| 9,782,971 | B2 | 10/2017 | Vernon |
| 9,814,904 | B2 | 11/2017 | Jones |
| 9,878,554 | B1 | 1/2018 | Komplin |
| 9,907,734 | B2 | 3/2018 | Rabe |
| 9,924,875 | B2 | 3/2018 | Rabe |
| 9,925,362 | B2 | 3/2018 | Rabe |
| 9,928,591 | B2 | 3/2018 | Rabe |
| 9,949,547 | B2 | 4/2018 | Rabe |
| 9,949,552 | B2 | 4/2018 | Rabe |
| 9,955,769 | B2 | 5/2018 | Rabe |
| 9,962,532 | B2 | 5/2018 | Rabe |

(Continued)

FOREIGN PATENT DOCUMENTS

| | | |
|---|---|---|
| AU | 2014200087 A1 | 1/2014 |
| CN | 107521229 B | 5/2019 |
| DE | 10153249 A1 | 5/2003 |
| DE | 202004003148 U1 | 3/2005 |
| ES | 2452530 T3 | 4/2014 |

(Continued)

OTHER PUBLICATIONS

U.S. Appl. No. 16/006,920, filed Jun. 13, 2018, Lingoes et al.
U.S. Appl. No. 16/006,944, filed Jun. 13, 2018, Meschkat et al.
International Search Report and Written Opinion for PCT/US2018/037227 dated Jun. 13, 2018.

(Continued)

*Primary Examiner* — Zohreh A Fay
(74) *Attorney, Agent, or Firm* — Melissa G Krasovec

(57) ABSTRACT

An array of cosmetic compositions intended to camouflage imperfections on human skin in a targeted manner is provided. The array includes two or more different cosmetic compositions, each cosmetic composition having a metal oxide. The different cosmetic compositions each have an L* value within the range of from about 60 to about 90. In addition, one or more of the cosmetic compositions from the array will effectively camouflage imperfections on a consumer's skin if they have an average skin L* value between 35 and 75.

15 Claims, 4 Drawing Sheets

(56) References Cited

U.S. PATENT DOCUMENTS

| | | | |
|---|---|---|---|
| 10,016,046 B2 | 7/2018 | Edgar | |
| 10,035,355 B2 | 7/2018 | Komplin | |
| 10,043,292 B2 | 8/2018 | Edgar | |
| 10,092,082 B2 | 10/2018 | Edgar | |
| 10,117,500 B2 | 11/2018 | Samain | |
| 10,163,230 B2 | 12/2018 | Edgar | |
| 10,166,799 B2 | 1/2019 | Rabe | |
| 10,188,192 B2 | 1/2019 | Rabe | |
| 10,188,193 B2 | 1/2019 | Rabe | |
| 10,238,582 B2 | 3/2019 | Rabe | |
| 10,265,260 B2 | 4/2019 | Giron | |
| 10,314,378 B2 | 6/2019 | Rabe | |
| 10,391,042 B2 | 8/2019 | Lingoes | |
| 10,449,773 B2 | 10/2019 | Komplin | |
| 10,467,779 B2 | 11/2019 | Edgar | |
| 10,486,174 B2 | 11/2019 | Edgar | |
| 10,511,777 B2 | 12/2019 | Nichols | |
| 10,553,006 B2 | 2/2020 | Iglehart | |
| 10,576,746 B2 | 3/2020 | Higuchi | |
| 2002/0155069 A1 | 10/2002 | Pruche | |
| 2003/0060810 A1 | 3/2003 | Syrowicz | |
| 2004/0073186 A1 | 4/2004 | Cameron | |
| 2004/0186373 A1 | 9/2004 | Dunfield | |
| 2004/0223985 A1 | 11/2004 | Dunfield | |
| 2005/0053628 A1 | 3/2005 | Montanari | |
| 2006/0077405 A1 | 4/2006 | Topfer et al. | |
| 2007/0035815 A1 | 2/2007 | Edgar | |
| 2007/0047761 A1 | 3/2007 | Wasilunas | |
| 2008/0037087 A1 | 2/2008 | Sugita | |
| 2008/0069620 A1 | 3/2008 | Anderson | |
| 2008/0070328 A1 | 3/2008 | Omura | |
| 2008/0080766 A1 | 4/2008 | Payonk | |
| 2008/0155467 A1 | 6/2008 | Obita | |
| 2008/0193195 A1 | 8/2008 | Edgar | |
| 2008/0194971 A1 | 8/2008 | Edgar | |
| 2009/0025747 A1 | 1/2009 | Edgar | |
| 2011/0124989 A1 | 5/2011 | Edgar | |
| 2011/0129283 A1 | 6/2011 | Samain | |
| 2011/0159463 A1 | 6/2011 | Samain | |
| 2011/0229247 A1 | 9/2011 | Song | |
| 2013/0149365 A1 | 6/2013 | Rajagopal | |
| 2013/0302078 A1 | 11/2013 | Edgar | |
| 2014/0010769 A1 | 1/2014 | Lomakin | |
| 2015/0182757 A1 | 7/2015 | Levine | |
| 2015/0196109 A1 | 7/2015 | Edgar et al. | |
| 2015/0297471 A1 | 10/2015 | Sunkel | |
| 2015/0359315 A1 | 12/2015 | Rabe | |
| 2015/0359712 A1 | 12/2015 | Rabe | |
| 2015/0359714 A1 | 12/2015 | Rabe | |
| 2016/0022972 A1 | 1/2016 | Rabe | |
| 2016/0360858 A1 | 12/2016 | Rabe | |
| 2016/0361526 A1 | 12/2016 | Rabe | |
| 2017/0157963 A1 | 6/2017 | Rabe | |
| 2017/0256084 A1 | 9/2017 | Iglehart | |
| 2018/0001646 A1 | 1/2018 | Vernon | |
| 2018/0279843 A1 | 10/2018 | Paul | |
| 2018/0310693 A1 | 11/2018 | Edgar | |
| 2018/0360190 A1 | 12/2018 | Villalobos Lingoes | |
| 2018/0360196 A1 | 12/2018 | Meschkat | |
| 2018/0368727 A1 | 12/2018 | Heath | |
| 2019/0080451 A1 | 3/2019 | Iglehart | |
| 2019/0193443 A1 | 6/2019 | Wong | |
| 2019/0209425 A1 | 7/2019 | Lee | |
| 2019/0263127 A1 | 8/2019 | Tanioku | |

FOREIGN PATENT DOCUMENTS

| | | |
|---|---|---|
| FR | 2933585 B1 | 10/2011 |
| JP | 2003052642 A | 2/2003 |
| JP | 2006271654 A | 10/2006 |
| JP | 2006297691 A | 11/2006 |
| JP | 2007001980 A | 1/2007 |
| JP | 2015120640 A | 7/2015 |
| WO | WO2006092604 A2 | 9/2006 |
| WO | 2008010628 A1 | 1/2008 |
| WO | 2008098234 A3 | 11/2008 |
| WO | 2009036876 A1 | 3/2009 |
| WO | 2009036924 A8 | 7/2009 |
| WO | 2009036925 A8 | 7/2009 |
| WO | 2010004528 A1 | 1/2010 |
| WO | 2010004531 A1 | 1/2010 |
| WO | 2010077703 A1 | 7/2010 |
| WO | 2011067761 A1 | 6/2011 |
| WO | WO2011078903 A1 | 6/2011 |
| WO | 2012103048 A3 | 10/2012 |
| WO | WO2015191821 A2 | 12/2015 |
| WO | WO2015191824 A2 | 12/2015 |
| WO | WO2016014886 A1 | 1/2016 |
| WO | 2018088594 A1 | 5/2018 |
| WO | 2018185773 A1 | 10/2018 |

OTHER PUBLICATIONS

International Search Report and Written Opinion for PCT/US2018/037230 dated Aug. 22, 2018.

International Search Report and Written Opinion for PCT/US2018/037511 dated Aug. 22, 2018.

All Office Actions for U.S. Appl. No. 16/006,944, filed Jun. 13, 2018.

All Office Actions for U.S. Appl. No. 16/006,920, filed Jun. 13, 2018.

"Illuminating Lights Face Palette", Database Accession No. 8249393, MINTEL, Nov. 5, 2020, 3 pages.

ARRAY OF COSMETIC COMPOSITIONS FOR CAMOUFLAGING TONAL IMPERFECTIONS

FIELD OF THE INVENTION

The present application relates to an array of cosmetic compositions intended to camouflage tonal imperfections on keratinous surfaces and more particularly, an array of cosmetic compositions that are designed to hide skin imperfections on the entire range of global skin tones by using targeted precision deposition techniques and very narrow range of shades when compared to existing cosmetic solutions.

BACKGROUND OF THE INVENTION

Cosmetic and skin care products that are designed to even out skin tone are commonplace. Examples of such products are cosmetic foundations, combination skin and cosmetic products like "BB" and "CC" creams, tinted moisturizers, and the like. These products come in many different forms. These forms can include liquids, creams and gels, creamy compacts, pressed and loose powders, and atomized sprays. These products are designed to even out skin tone by covering the imperfections with a composition designed to match the color of the user's skin. However, due to the wide range of human skin tones, a multitude of shades is needed in order to meet the needs of users across ethnicities, ages, and geographies. The higher the opacity of the product, the more shades that are required in order for the product to be useful over the wide spectrum of human skin tones. Lower opacity products like "BB" and "CC" creams and tinted moisturizers are commonly sold in 3 to 5 different shades. Higher opacity products like foundations are commonly sold in 12 to 30 different shades.

In addition, the more coverage of the imperfection these traditional products provide, the less natural the skin appearance can become. This unnatural appearance can be caused by multiple factors. Firstly, government regulatory agencies around the globe have created a limited list of colorants that are approved for use on human skin. This approved list of colorants has fundamental limitations in how closely they can create a visible wavelength spectral reflectance profile that perfectly matches that of human skin. This forces users to try to get as close as possible to their skin color. However, the skin color match is rarely close enough for the product to appear invisible on the skin. Second, traditional products are fundamentally monochromatic. Even the most flawless looking skin is still composed of a multitude of shades across the face. Thus, the more coverage of the underlying skin, the more monochromatic the skin can become and the less natural it can appear. A third cause of this unnatural appearance is the manner in which light reflects from the surface of bare skin versus the way light reflects from a pigmented film formed by the product on the skin. Skin innately has a complex interaction with visible light. Part of the light is reflected from the upper layers of the stratum corneum while part of the light penetrates through the stratum corneum into the dermal and collagen layers before reflecting back out of the skin. Yet another portion of light laterally diffuses through the collagen layer before reflecting back out. In general, the amount of light reflected from below the surface of the skin can be correlated to a desirable skin attribute that consumers often refer to as "radiance". With current traditional skin evening products, the more coverage and skin evening they impart, the less light they allow to penetrate into the skin. This gives an unnatural visual effect as more of the light is reflecting off of the pigmented film on the surface of the skin, leading to a "flat" mannequin-like look.

In addition, current cosmetic compositions rely on color-matching the skin to attempt to hide tonal skin imperfections. This results in two undesirable options. First, the cosmetic foundations available in an array are not an exact match for the consumer's skin tone, resulting in an unsatisfactory result. Alternatively, a very large array of cosmetic foundations is offered in which a consumer will have great difficulty in finding the correct match.

Therefore, a need still exists for an array of cosmetic compositions that will effectively camouflage tonal imperfections for any consumer while presenting a fairly narrow range of options, making the selection process less onerous.

SUMMARY OF THE INVENTION

An array of cosmetic compositions intended to camouflage imperfections on human skin in a targeted manner is provided. The array includes two or more different cosmetic compositions, each cosmetic composition having a metal oxide. The metal oxide may be zinc oxide, iron oxide, titanium oxide or a mixture. The different cosmetic compositions each have an L* value within the range of from about 60 to about 90. In addition, one or more of the cosmetic compositions from the array will effectively camouflage imperfections on a consumer's skin if they have an average skin L* value between 35 and 75.

In one embodiment, the L* value for each of the cosmetic compositions is within the range of from about 65 to about 85. In another embodiment, the L* value for each of the cosmetic compositions is within the range of from about 65 to about 85, and one or more of the cosmetic compositions from the array will effectively camouflage imperfections on a consumer's skin if the consumer has an average skin L* value between 35 and 75.

In one embodiment, the two or more different cosmetic compositions each have an opacity of at least 0.2. In another embodiment, the two or more different cosmetic compositions each have an opacity of from about 0.2 to about 1. In yet another embodiment, the two or more different cosmetic compositions each have an opacity of 0.25 to about 1.0. In one embodiment, the two or more different cosmetic compositions each have an opacity of 0.3 to about 1.0.

In another embodiment, the two or more different cosmetic compositions each have a C* value, and the C* value for each of the cosmetic compositions is within the range of from about 15 to about 45. In one embodiment, the C* value for each of the cosmetic compositions is within the range of from about 20 to about 40.

In one embodiment, the two or more different cosmetic compositions each have an h* value, and the h* value for each of the cosmetic compositions is within the range of about 50 to about 80.

In another embodiment, the metal oxide has a particle size from about 100 nm to about 50 microns. In one embodiment, the metal oxide has a particle size from about 200 nm to about 10 microns.

In one embodiment, the array comprises from about two to about ten different cosmetic compositions. In another embodiment, the array comprises from about three to about seven different cosmetic compositions. In one embodiment, array comprises four different cosmetic compositions.

BRIEF DESCRIPTION OF THE DRAWINGS

While the specification concludes with claims particularly pointing out and distinctly claiming the present invention, it is believed the same will be better understood from the following description taken in conjunction with the accompanying drawings in which:

DETAILED DESCRIPTION

Figure 1:
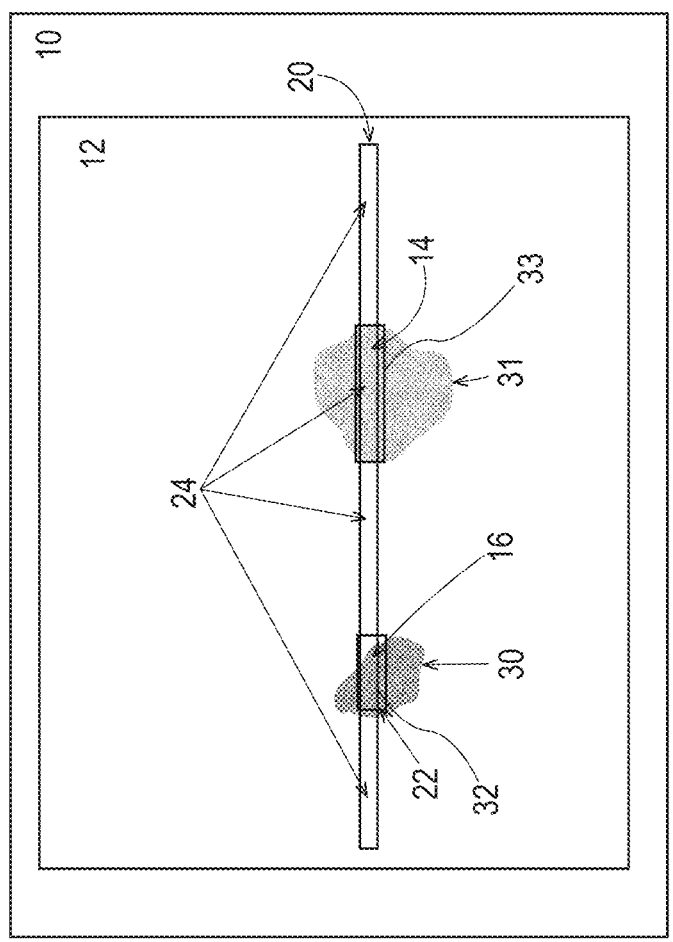
FIG. 1 is a schematic representation of an analytical window according to the present invention wherein skin is analyzed by a deposition device useful in the present invention.

As used herein "basal skin" refers to bare skin free of cosmetics, skin care products, or other compositions.

As used herein "camouflage" means to hide or make a tonal imperfection less visible by seamlessly blending it with the surrounding keratinous surface. A keratinous surface can be human skin and/or hair.

As used herein "CIE (Commission internationale de l'éclairage) L*C*h*" or "CIELCh" is a color space specified by the International Commission on Illumination. It describes all the colors visible to the human eye and was created to serve as a device-independent model to be used as a reference. "L*C*h*" refers to the commonly known color model represented by a three-dimensional 1976 CIE color space. L*C*h* is the cylinder whose axes are defined by the dimensions of lightness value (L*), chroma value (C*) and hue value (h*). Color values are reported at D65/10° lighting/observer unless noted otherwise.

As used herein, "chroma" refers to the quality of a color's purity, intensity or saturation.

As used herein, "chroma value" (C*) refers to the position in the CIELCh color space in the range from 0 at the center of the circle, which is completely unsaturated (i.e. a neutral grey, black or white), to 100 or more at the edge of the circle, which is completely saturated. A color having a high chroma value is vivid, almost completely free of white, while a color having a low chroma value is dull, washed-out, and pale in appearance.

As used herein, the term "effectively camouflage" means to camouflage a tonal imperfection such that the tonal imperfection is not perceivable by the human eye without the aid of magnifying apparatuses.

As used herein, "hue" refers to what is commonly called color, i.e., red, green, blue-green, orange, etc.

As used herein, "hue value" (h*) refers to the position on a circular axis that an object can be described in CIELCh color space in the form of degrees (°) (or angles), ranging from 0° (red) through 90° (yellow), 180° (green), 270° (blue) and back to 0°.

As used herein, "lightness" is a representation of variation in the perception of a color or color space's brightness.

As used herein "lightness value" (L*) refers to the vertical position in the CIELCh color space from 0, which has no lightness (i.e. absolute black) at the bottom, through 50 in the middle, to 100, which is maximum lightness (i.e. absolute white) at the top.

As used herein "shade" refers to the combination of L*C*h* values for a particular object (e.g. skin or composition).

As used herein "targeted deposition" refers to the delivery of a composition substantially only onto the tonal imperfection to correct and/or change the color of the tonal imperfection to match the surrounding keratinous surface.

As used herein "tonal imperfection" refers to an area of keratinous surface which is different in color, typically darker, than the surrounding keratinous surface.

As used herein, the articles "a" and "an" are understood to mean one or more of the material that is claimed or described.

All weights, measurements and concentrations herein are measured at 23° C. and 50% relative humidity (RH), unless otherwise specified.

All percentages, parts and ratios as used herein are by weight of the total composition, unless otherwise specified. All such weights as they pertain to listed ingredients are based on the active level and, therefore do not include solvents or by-products that may be included in commercially available materials, unless otherwise specified.

The present invention provides an array of cosmetic compositions that are designed to hide skin imperfections on the entire range of global skin tones by using targeted precision deposition techniques and a narrow range of shades when compared to existing cosmetic solutions. The cosmetic compositions of the array can be utilized by users who have a variety of skin lightness, chroma, and/or hues. In one aspect, precise deposition of a pigmented cosmetic composition comprising a particular set of L*C*h* values can result in natural, flawless looking skin, while still remaining substantially undetectable to the naked eye.

Included are embodiments of inventions that create precise deposition of a cosmetic formulation that camouflage skin imperfections while looking completely natural to the naked eye. The current invention is based on a fundamentally new deposition model that no prior embodiments can emulate. The first element of the new deposition model is that product is precisely placed only on the imperfections themselves (i.e., "targeted deposition"). Depending on the method of analysis and the consumer's level of imperfections the percentage of surface area that is targeted with cosmetic varies, however most consumers can achieve dramatic skin evening by targeting and depositing onto less than 20% of the skin. This leaves more than 80% of the skin bare which dramatically improves the natural appearance of skin as the light is able to interact naturally with the majority of the skin without interference from the cosmetic film. The second element of the new deposition model is that the cosmetic product itself is not intended to match the shade of the consumer's skin. When placed precisely only on the imperfection it is possible to use the cosmetic product to shift the lightness and darkness of the imperfection rather than to completely hide the imperfection. Visual color space is most accurately measured using a spectrometer that can graph the amount of reflectance across the visible spectral frequencies of 400-700 nm. One mathematical representation of the spectral profile is through use of a color standard like CIE LCh color space which is designed to represent how the human eye sees color. In the CIE LCh color standard L is the degree of lightness, C is the chroma (the intensity of the color) and h is the hue angle (0-360). It is possible to camouflage imperfections by precisely targeting and depositing opaque product that is lighter than the color of the background skin and to lift the spot's lightness to match that of the average skin lightness. However, since previous disclosures were conducted with a very small portion of the global skin color population, only a narrow range of products were used. What was not understood was the range of LCh of products that would be needed to be to meet the total range of global skin tones. The present invention has identified a very specific range of LCh of products that are needed to hide tonal skin imperfections for all consumers so that they appear invisible to the naked eye.

As has been discussed, all current skin care and cosmetic products designed to hide skin imperfections are designed to have an LCh of the product match as close to the LCh of the skin tone as possible. Therefore the range of LCh of the products matches the range of LCh of global consumers. As such, the range of shades for currently available products that are designed to hide imperfections is huge, making shade selection a very difficult task. The present invention has found a solution to this problem.

All human skin is composed of the same building blocks that create its visual macroscopic color: melanin, oxygenated hemoglobin, un-oxygenated hemoglobin, and collagen. These building blocks are combined in a wide variety of manners to form different skin tones. The range of skin lightness, or L* using the CIE LCh color standard, across all geographies and ethnicities has been found to be approximately 35-75 It is also known that human skin has an h* value of about 30 to about 75, and a C* value of about 5 to about 30. These building blocks are combined in a wide variety of manners across different ethnicities, ages and geographies.

As has been discussed the range of human skin tones has been studied in numerous research activities. Due to the current technical model of hiding skin imperfections shared by all existing cosmetics the range of lightness of offered is similarly broad. One of the many examples would include L'Oreal True Match liquid form foundation which has one of the largest range of shades of any commercial foundation product which offers 33 "skin true" shades. All of the LCh colors are measured using a dried down film rather than a wet product measurement as the dried product represents the state that the product will exist on skin post application by a consumer and is therefore most relevant. In this product range the lightest shade is W1 "Porcelain" which has an L* value of 79 a C* value of 21 and a h* value of 62. The darkest shade in the product line is C10 "Espresso" which has an L* value of 32 a C* value of 12 and an h* value of 46. Thus the range of L values of the product offering is closely matched to that of all human skin tones. Another example of commercially available foundations is Mac creamy compact form "Full Coverage Foundation" which offers 16 shades and is claimed to be "A foundation that's both water-resistant and long-wearing with opaque coverage." In this product line the lightest product shade is "NC15" which has an L* value of 74 a C* value of 20 and an h* value of 61. The darkest shade in the product line is "NW50" which has an L* value of 40 a C* value of 22 and an h* value of 54. In yet another example of commercially available cosmetics designed to hide tonal imperfections is a lower coverage product range like Bobby Brown's "BB Cream SPF 35" line of products which comes in 9 shades. In this product line the lightest shade is "Extra Light" which has an L* value of 71 a C* value of 23 and an h* value of 60. The darkest shade in the product line is "Deep" which has an L* value of 38 a C* value of 32 and an h* value of 53. As has been shown in each of these examples the shade range of the cosmetic products are all designed to have a shade range similar to that of human skin.

The current invention discloses an array of products that are applied via a precise targeted deposition method that applies cosmetic only to the tonal imperfections and utilizes a range of shades that does not mirror that of the range of human skin tones. Because the product is precisely applied to the only the hyper-pigmented areas of skin it enables a new method of correcting skin imperfections. This method applies a product significantly lighter than that of the skin in order to lift the lightness of the spot to match that of the surrounding skin. The present invention has identified the product shade range needed to correct the imperfections of the entire range of global skin shades. Surprisingly it was found that the range of product shades that is able to best correct the tonal imperfections of the entire range of human skin shades is a much narrower range of shades than any current cosmetic product range.

As has been previously disclosed in US2015360016A1 there is a new way to correct skin imperfections, particularly hyperpigmentation, in which you precisely deposit a composition that is significantly lighter in shade than the basal skin. Previous disclosures of targeted deposition did not recognize the role of chroma and hue of the applied composition across a wide range of skin tones would need to be in order to correct the imperfection in a manner that makes it macroscopically invisible to the naked eye. The present invention involved testing a wide range of product shades and consumer skin tones and determined that there are specific ranges of LCh values of product that best correct consumers with specific ranges of skin LCh in order to enable the precisely targeted depositions to be invisible to the naked eye. Moreover it has been discovered that this range of shades, unlike conventional cosmetic products is much narrower than that of the range of global skin tones.

It is known that one has to match the chroma and hue of human skin in order to give the appearance of natural skin when using a foundation or similar product. It was surprisingly found that matching the shade, or L*C*h* values, of a pigmented cosmetic composition to the skin tone is not required, but rather it is preferable to adjust the shade of the composition according to variable skin tones and imperfections with L*C*h* values that do not attempt to match the basal skin.

Targeted deposition techniques which precisely deposit a composition onto tonal imperfections in order to correct tonal imperfection are known. Such compositions can comprise a L* value higher than the user's basal skin. However, the maximum range of L* values for compositions which can camouflage tonal imperfections across substantially the entire spectrum of skin tones was not known. In addition, the role of the C* value of the composition in the correction of tonal imperfections was not understood. In particular, it was unknown the C* value of the applied composition that was needed to correct tonal imperfections across a wide range of skin tones.

As skin tones vary across different populations and/or ages, the maximum delta (□) L*, calculated as the average composition L* value minus the average skin L* value, that is tolerable (i.e. not visible to the naked eye, yet still covers the imperfection) changes. If the □L* is too high, the composition can be visible and can appear ashy or white on the skin. This can occur on both dark and light skin tones.

It has been found that pigmented cosmetic compositions comprising an average composition L* value substantially greater than that the average L* value of the user can camouflage tonal imperfections in a manner that makes it macroscopically invisible to the naked eye and can be utilized across a wide range of skin tones. In one aspect, the pigmented cosmetic compositions can comprise an average composition L* value of between about 10 to about 40 units greater than the average skin L* value, preferably between about 15 to about 35 units greater, and even more preferably between about 20 to about 35 units greater. In one aspect, the pigmented cosmetic composition can have an average composition L* value of at least 10 units greater than the average skin L* value of the user, preferably at least 15 units greater, and even more preferably at least 20 units greater. The average skin L* value can be measured according to the LCh Test Method for Skin described hereafter. The average composition L* value can be measured according to the LCh Test Method for Compositions described hereinafter.

The pigmented cosmetic composition can also comprise an □C* between the composition and skin of the user of about 25 or less, alternatively less than about 20, alternatively less than about 18. The average □C* can be calculated as the average composition C* value minus the average skin C* value of the user. The difference between the average cosmetic C* value and the average skin C* value should increase as the user's average skin L* value decreases. In one aspect, the □C* can be from about 0 to about 14 for light and/or medium skin tones (for instance Fitzpatrick Scale Types I-IV), alternatively the □C* can be from about 0 to about 10. In another aspect, the □C* can be from about 8 to about 21 for medium-dark and/or dark skin tones (for instance Fitzpatrick Scale Types V-VI). The average skin C* value can be measured according to the LCh Test Method for Skin described hereafter. The average composition C* value can be measured according to the LCh Test Method for Compositions described hereinafter.

While not wishing to be bound by theory, it is believed that this combination of lightness and chroma is needed due to small list of colorants that are FD&C approved for use on human skin, thus limiting the use of pigmentary grade titanium dioxide for high opacity formulas. It was found that titanium dioxide has a blue component that becomes more obvious on darker skin tones, thus a higher chroma component is needed to offset the color shift on darker skin.

In one aspect, the pigmented cosmetic compositions can comprise multiple shades with one having an average composition L* value from about 85 to about 80, another from about 79 to about 75, and yet another from about 74 to about 65.

In one aspect, the pigmented cosmetic compositions can comprise multiple shades with one having an average composition C* value of from about 40 to about 35, another from about 34 to about 30, another yet from about 29 to about 20.

In one aspect, the pigmented cosmetic compositions can comprise multiple shades with one having an average composition h* value of from about 80 to about 70, another from about 69 to about 60, and yet another from about 59 to about 50. The average composition h* value can be measured according to the LCh Test Method for Compositions described hereinafter.

Any combination of opacifiers and colorants can be used to obtain the desired shade of the pigmented cosmetic composition. One skilled in the art would understand how to formulate a pigmented cosmetic composition using a range of pigments to arrive at the desired L*C*h* values. Inks, dyes, metal oxides and pigments (collectively referred to as "colorants" hereinafter) can be used to modify the color or reflectance of the skin. Opacifier and colorant combinations should be used in a range of particle sizes and viscosities that can be deposited efficiently on human skin.

In one aspect, a method of camouflaging a tonal imperfection can comprise the steps of:
a. identifying a skin tone of a user comprising a tonal imperfection;
b. instructing a user to select a pigmented cosmetic composition adapted to camouflage a tonal imperfection based on the user's skin tone;
c. optionally providing a guide to the user that allows the user to select the pigmented cosmetic composition, wherein the pigmented cosmetic composition is available in different shades and the guide recommends a specific shade;
d. selecting the pigmented cosmetic composition;
e. selectively targeting and depositing the selected pigmented cosmetic composition onto the tonal imperfection;
wherein the pigmented cosmetic composition comprises an average composition L* value of about 10 to about 40 units greater than an average skin L* value of the user.

The skin tone of a user can be identified by the LCh Test Method for Skin, as described hereinafter, by Fitzpatrick Scale, by comparing a user's skin to a color guide comprising images and/or descriptions of different skin tones, by taking a picture of the user's skin and analyzing the skin tone, by measuring using a tool such as a Sephora Color IQ or SKII Magic Ring, or other equivalent approaches. In one aspect, the skin tone of a user can be identified based on ethnicity.

The Fitzpatrick scale (also commonly referred to as the "Fitzpatrick skin typing test" or "Fitzpatrick phototyping scale") is a numerical classification schema for human skin color developed in 1975 by Thomas B. Fitzpatrick. It is a way to estimate the response of different types of skin to ultraviolet (UV) light, based on the user's report of how their skin responds to the sun (i.e. burning and tanning). The Fitzpatrick Scale is a recognized tool for dermatological research into human skin pigmentation. The following list shows the six skin types on the Fitzpatrick Scale. Scores are based on standard questions that assign a number to eye, hair, and skin color, amount of freckles, sensitivity to the sun (i.e. burning versus tanning) and the timeframe of the last sun exposure.

Type I (scores 0-6) always burns, never tans (pale white; blond or red hair; blue, gray eyes; freckles);
Type II (scores 7-13) usually burns, tans minimally (white; fair; blond, brown or red hair; blue, green, or hazel eyes);
Type III (scores 14-20) sometimes mild burn, tans uniformly (cream white; yellowish; fair with any hair color or brown eyes);
Type IV (scores 21-27) burns minimally, always tans well (light brown; olive; dark brown to black hair);
Type V (scores 28-34) very rarely burns, tans very easily (brown); and
Type VI (scores 35-36) never burns, always tans (deeply pigmented dark brown to darkest brown, black in complexion).

Fitzpatrick Scale types are known to be correlated with the L* value of human skin tones. (See Lee, J. A., Osmanovic, S., Viana, M. A. G., Kapur, R., Meghpara, B., & Edward, D. P. "Objective Measurement of Periocular Pigmentation." *Photodermatology, Photoimmunology & Photomedicine,* 24.6 (2008): 285-290). An average skin L* value of greater than about 55 can correspond to a Fitzpatrick Scale Type I to IV. An average skin L* value of less than or equal to about 55 can correspond to a Fitzpatrick Scale Type V and VI.

In one aspect, a user can be asked one or more questions to determine what skin type she is on the Fitzpatrick Scale. In one aspect, the user can be shown a range of printed or digitally displayed shades that are calibrated to the six Fitzpatrick Scale Types and can be instructed to place them against her own skin and to pick the corresponding Fitzpatrick Scale Type that is closest to her own skin color. In another aspect, the user can be asked which shade of makeup she currently uses and can be provided a cross reference guide which groups common makeup shades and brands against the corresponding closest Fitzpatrick Scale Type.

Instructions can be provided to the user on how to select the shade of the pigmented cosmetic composition based on the user's skin tone. In one aspect, when the user has a particular skin tone or Fitzpatrick type, the instructions can direct the user to select a particular pigmented cosmetic composition. For instance, if the user has a Fitzpatrick Type I-IV, the instructions can direct the user to select a light and/or medium shade. Alternatively, if the user has a Fitzpatrick Type V-VI, the instructions can direct the user to select a medium-dark and/or dark shade. In one aspect, when the user has a skin Fitzpatrick Type I, II, III, or IV, the pigmented cosmetic composition should have an average composition L* value of from about 75 to about 85 and/or an average composition C* value of about 22 to about 39. In one aspect, when the user has a skin Fitzpatrick Type V or VI, the pigmented cosmetic composition should have an average composition L* value of from about 65 to about 74 and/or an average composition C* value of about 30 to about 40.

Guidance can be provided to help the user or a beauty consultant select the pigmented cosmetic composition that will best camouflage the tonal imperfection. The pigmented cosmetic composition can be available in different shades and the guide can recommend a specific shade that can be used with a deposition device. In one aspect, the pigmented cosmetic composition can come in an array of four different shades which can be utilized by users across all Fitzpatrick Scale Types.

Guidance can come in the form of text, images, a color chart on a pamphlet, package, store shelf, end-cap, and/or display, that indicates what shade of pigmented cosmetic composition a user should pick based on her skin tone. Alternatively, guidance can come from a person working at a store or beauty counter or a dermatologist, alternatively guidance can come in the form of examples of the Fitzpatrick Scale types and the corresponding shades that match the given Fitzpatrick Type. In one aspect, the text or image can describe an ethnicity and direct the user to select a shade based on her ethnicity.

The user can apply the selected pigmented cosmetic composition onto the tonal imperfection using a deposition device. When placed on the tonal imperfection, it is possible to use the pigmented cosmetic composition to shift the lightness, chroma, and/or hue of the tonal imperfection rather than to completely hide the tonal imperfection. This approach to camouflaging tonal imperfections is possible when the pigmented cosmetic composition is deposited precisely and substantially only onto the tonal imperfection and has a very fine level of dosage variability. In one aspect, the pigmented cosmetic composition need not be deposited onto the entire face or body. It is believed that if the pigmented cosmetic composition is deposited on the surrounding skin and not just the tonal imperfection, the skin will have an ashy or white appearance. Thus, the deposition of the pigmented cosmetic composition is preferably delivered by a device that can meter out picoliters of the composition rather than the microliter quantities typically applied from traditional personal care applicators.

In one aspect, the deposition device can precisely target and deposit the pigmented cosmetic composition onto the tonal imperfection. The pigmented cosmetic composition can be deposited onto the tonal imperfection by any means so long it targets the tonal imperfection while leaving the surrounding skin substantially free of the pigmented cosmetic composition. In one aspect, the pigmented cosmetic composition can be deposited onto the tonal imperfection via a kit for deposition by hand that aids the user in depositing small amounts of the pigmented cosmetic composition substantially only onto the tonal imperfection. In another aspect, the pigmented cosmetic composition can be deposited onto the tonal imperfection via a deposition device such as by inkjet deposition such as thermal inkjet or piezo inkjet systems, direct contact using precision dabbing or stamping tools, atomized spray deposition, and combinations thereof. Though many different types of automated application devices can be used, one preferred method of depositing the pigmented cosmetic composition utilizes inkjet deposition.

An exemplary deposition device can analyze skin tonal imperfections and deposit the pigmented cosmetic composition when a tonal imperfection is identified. In one aspect, the deposition device can take at least one image of at least 10 $\mu m^2$ of skin and then calculate the average background lightness of the image on a grey scale (lightness value on a grey scale is herein referred to as "L value"). Further, from the same image, a localized L value can be calculated for individual pixels or a group of pixels. The local L value can then be compared to the background L value to identify skin deviations. A tonal imperfection is an area of skin where the absolute value of the difference between a local L value and the background L, (this difference being defined as "$\Delta L_M$" or the measured $\Delta L$, "$\Delta$" is commonly defined as the symbol for a difference between two values) is greater than a predetermined $\Delta L_S$ (wherein the "S" refers to a set $\Delta L$). The background L can be preset, or calculated by a variety of methods described below. The tonal imperfection is then treated with the pigmented cosmetic composition having a predetermined or variable contrast ratio.

One characteristic of the pigmented cosmetic compositions of the present invention is the contrast ratio. The contrast ratio of the pigmented cosmetic composition when depositing it onto a surface like skin is preferably between 0.1 and 1.0, more preferably between 0.2 and 1.0, and most preferably between 0.3 and 1.0. Herein, "contrast ratio" refers to the opacity of the pigmented cosmetic compositions of the present invention, or the ability of the composition to reduce or prevent light transmission, determined after the composition is drawn onto an opacity chart (Form N2A, Leneta Company of Manwah, N.J. or the equivalent thereof) and by using a spectrophotometer with settings selected to exclude specular reflection. The composition is diluted with a 1% Stabylen 30 in DI water premix at a 10:1 ratio. It is applied to the top of the opacity chart and then is drawn into a film having a thickness of approximately 0.01 inches using a film applicator (e.g., as commercially available from BYK Gardner of Columbia, Md., or the equivalent thereof). The film is allowed to dry for 2 hours under conditions of 22° C.+/−1° C., 1 atm. Using a spectrophotometer, the Y tristimulus value (i.e., the XYZ color space of the film) of the film is measured and recorded. The Y tristimulus value is measured in three different areas of the film over the black section of the opacity chart, and also in three different areas of the film over the white section of the opacity chart.

The background L can be calculated anywhere within the image. The image is taken where the nozzles will fire the pigmented cosmetic composition. The background L can be the arithmetic average, median, or mean of a plurality of local Ls, which means the calculation can include all of the local Ls in the image, or a subset thereof.

Referring now to FIG. 1, where analytical window 10 is an area that comprises a sample of skin 12 and nozzle array 20. The analytical window can be any shape including circular, square, rectangular, triangular, a parallelogram, or a polygon. Nozzle array 20 can contain one or more nozzles 24 that are off, or not firing, and one or more nozzles 22 that are on, or firing. Tonal imperfection 30 is shown underneath nozzle array section 32 and skin region 31 is shown underneath nozzle array region 33. Background L is calculated on and around skin 12, skin area 14 is where local $L_1$ is measured, and skin area 16 is where local $L_2$ is measured. Skin area 14 is under nozzle array 20 but not within a tonal imperfection. Thus, the absolute value of local $L_1$–background L ($\Delta L_{1M}$) is less than the preset threshold to initiate nozzle firing. The $\Delta L_S$ threshold required to initiate nozzle firing is a variable and is dependent on the scale used. For example, in a case where the 0-255 gray scale is utilized then the $\Delta L_S$ threshold required to initiate nozzle firing would commonly be a value of 2 or greater. Thus, in the example shown in FIG. 1, the value of $\Delta L_{1M}$ is less than 2. Skin area 16 is within tonal imperfection 30, and the absolute value of local L2–background L ($\Delta L_{2M}$) is greater than about 2. Thus, the nozzles around skin area 14 are generally off, and the nozzles around skin area 16 are generally firing.

To insure the nozzles do not clog with particles or dried pigmented cosmetic composition, any nozzle can be fired at any time simply to keep it clean or clear, i.e., not blocked, and "healthy". The number of nozzles directly over a tonal imperfection that are fired in response to the tonal imperfection can be adjusted based on the size of $\Delta L_S$, the size (e.g., surface area) of the tonal imperfection or other parameters devised by those skilled in the art.

Treatment times will vary based on the size of the skin surface area that needs treatment and the precision and amount of the modification. For example, a woman may wish to simply touch up a few small areas on her face before going to the grocery store. This treatment might take a few minutes. Alternatively, a young bride might wear her wedding dress to a salon where a salon professional meticulously treats all exposed areas of skin prior to the wedding and the taking of her wedding pictures. This full body treatment might take hours. Accordingly, the user will have tremendous control over the amount of time they choose to use the present device.

Figure 2:
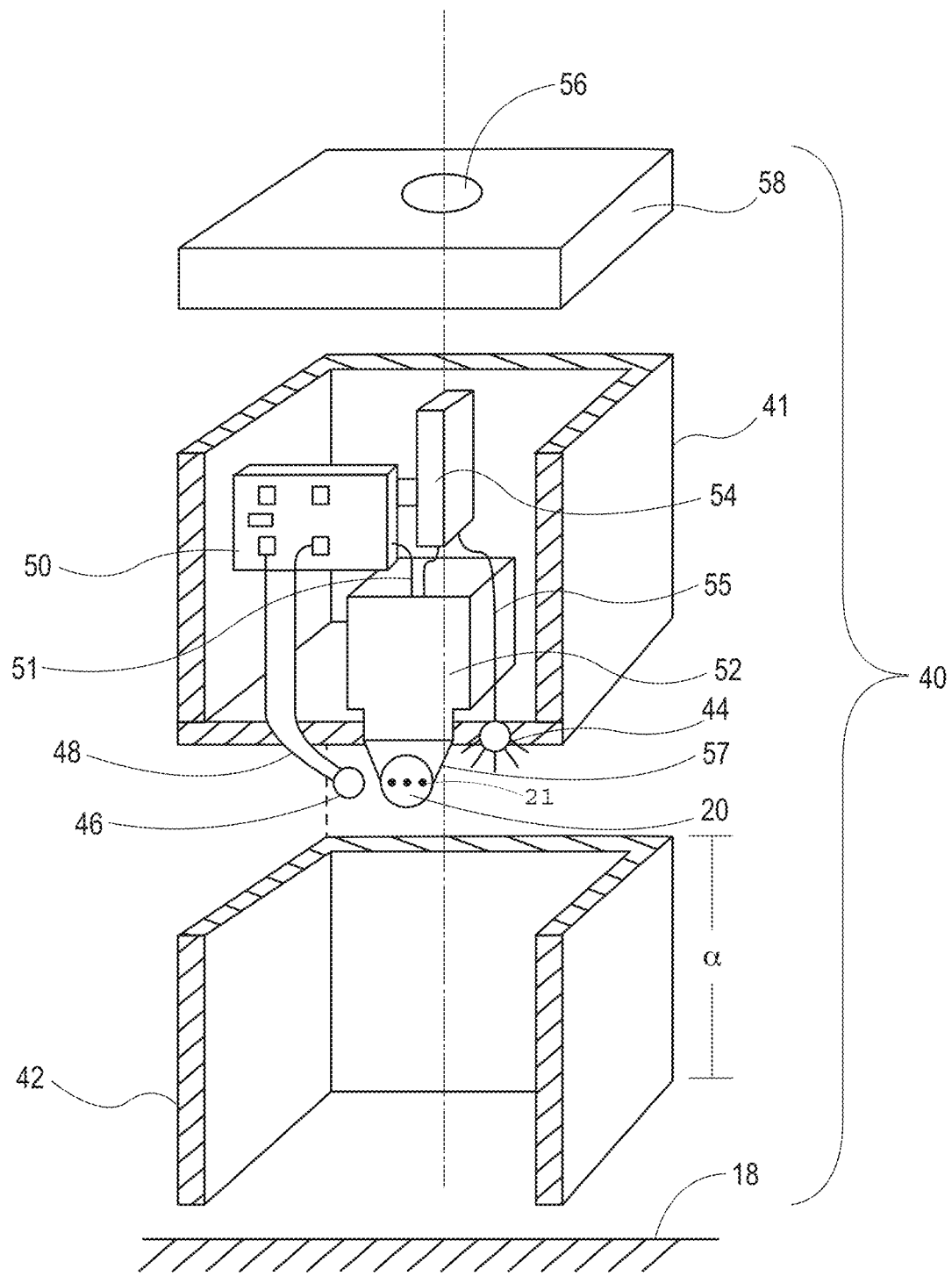
FIG. 2 is a deposition device useful in the present invention.

Referring now to FIG. 2, which shows deposition device 40 according to the present invention. Deposition device 40 is directly above skin 18, separated by physical spacer 42. Physical spacer 42 has a set, predetermined height a such that when it contacts skin 18, the mechanical and electrical elements are all at a known distance from skin 18. The mechanical and electrical elements are associated with deposition device 40 include, but are not be limited to, light 44, sensor 46, nozzle array 20 which is embedded on cartridge die 57 which is attached to printer cartridge 52. Cartridge die 57 is made of silicon, glass, machineable glass ceramic, sapphire, alumina, printed wiring board substrates (for example, FR4, Liquid Crystal Polymer, polyimide etc,) within which the nozzle array 20 can be formed. All of these elements are enclosed within optional apparatus housing 41.

Light 44 illuminates the area of skin 18 within spacer 42 such that sensor 46 has relatively constant illumination. Background lighting will affect the image capture as portions of spacer 42 lift off of skin 18 and allow background light in and the illumination from light 44 to escape, but small deviations in illumination can be corrected for provided light 44 provides a relatively constant background illumination. Light 44 can be a light emitting diode (LED), incandescent light, neon bulb based, or any other commercially available source of illumination. Light 44 can have constant illumination or adjustable illumination. For example, an adjustable light source might be useful if the background illumination is excessively bright or dark.

Sensor 46 can be any component that is capable of obtaining a visual property of an area of skin, non-limiting examples of which can include image capture devices, spectrophotometers, photonic measuring devices for wavelengths within the visible spectrum as well as those wavelengths above and below the visible spectrum which could measure sub-surface features, and combinations thereof.

In one aspect, sensor 46 can be an image capture device that is capable of taking images of the skin 18. The image capture device can be any of a variety of commercially available devices such as a simple camera or a digital cmos camera chip. Sensor 46 can take a measurement of the L value of skin 18 and/or can take an image of skin 18 and can send it to processor 50 via image capture line 48 for analysis. The image may be analyzed for local L values, background L values, or both. Grey scale conversion occurs within the analytical processing capabilities of processor 50. The comparison of background L to local L to determine the $\Delta L_M$ occurs within processor 50, which can be a commercially available programmable chip, or other commercially available processing units.

Processor 50 is generally referred to as a central processing unit ("CPU"). The CPU can be a single programmable chip like those found in consumer electronic devices such as a laptop computer, a cell phone, an electric razor, and the like. The CPU may comprise an Application Specific Integrated Circuit (ASIC), controller, Field Programmable Gate Array (FPGA), integrated circuit, microcontroller, microprocessor, processor, and the like. The CPU may also comprise memory functionality, either internal to the CPU as cache memory, for example Random Access Memory (RAM), Static Random Access Memory (SRAM), and the like, or external to the CPU, for example as Dynamic Random-Access Memory (DRAM), Read Only Memory (ROM), Static RAM, Flash Memory (e.g., Compact Flash or SmartMedia cards), disk drives, Solid State Disk Drives (SSD), or Internet Cloud storage. While it is anticipated that a remote CPU, either tethered to the deposition device or which communicates wirelessly, can be used, a local CPU within the deposition device is exemplified herein.

Images can be taken in sequence or preferably continuously. An image capture device that takes a minimum of 4 frames per second is preferred. Higher speed image capture devices (greater than 4 frames per second) are desired as well, for example greater 100 frames per second, alternatively greater than 200 frames per second, alternatively greater than 600 frames per second. All images can be taken in a grey scale or converted to a grey scale, and the grey scale can have any range, for example, 0-255, no units. This corresponds approximately to a refresh rate of 0.2 seconds or faster. Consistent with the image capture device, the CPU can process at a rate of 100 frames per second, alternatively greater than 200 frames per second, alternatively greater than 600 frames per second.

The results of the image analysis, when compared to criteria pre-programmed into processor 50, may result in a desired modification of skin 18. In such a case, for example when the calculated $\Delta L_M$ exceeds the pre-determined $\Delta L_S$, a signal is sent from processor 50 to cartridge 52, via cartridge line 51, to fire one or more nozzles 21 in nozzle array 20 and dispense a pigmented cosmetic composition.

Power for cartridge 52, light 44, sensor 46, processor 50, and other mechanical and electrical elements that might be present can be supplied by power element 54 via one or more power lines 55. Power element 54 can be turned off and on, which in turn turns deposition device 40 off and on, via power switch 56 which can be located anywhere on deposition device 40, but is shown here on device cover 58. Power element 54 may include energy storage functionality via a battery, a rechargeable battery, an electrochemical capacitor, a double-layer capacitor, a supercapacitor, a hybrid battery-capacitor system, and combinations thereof.

Figure 3:
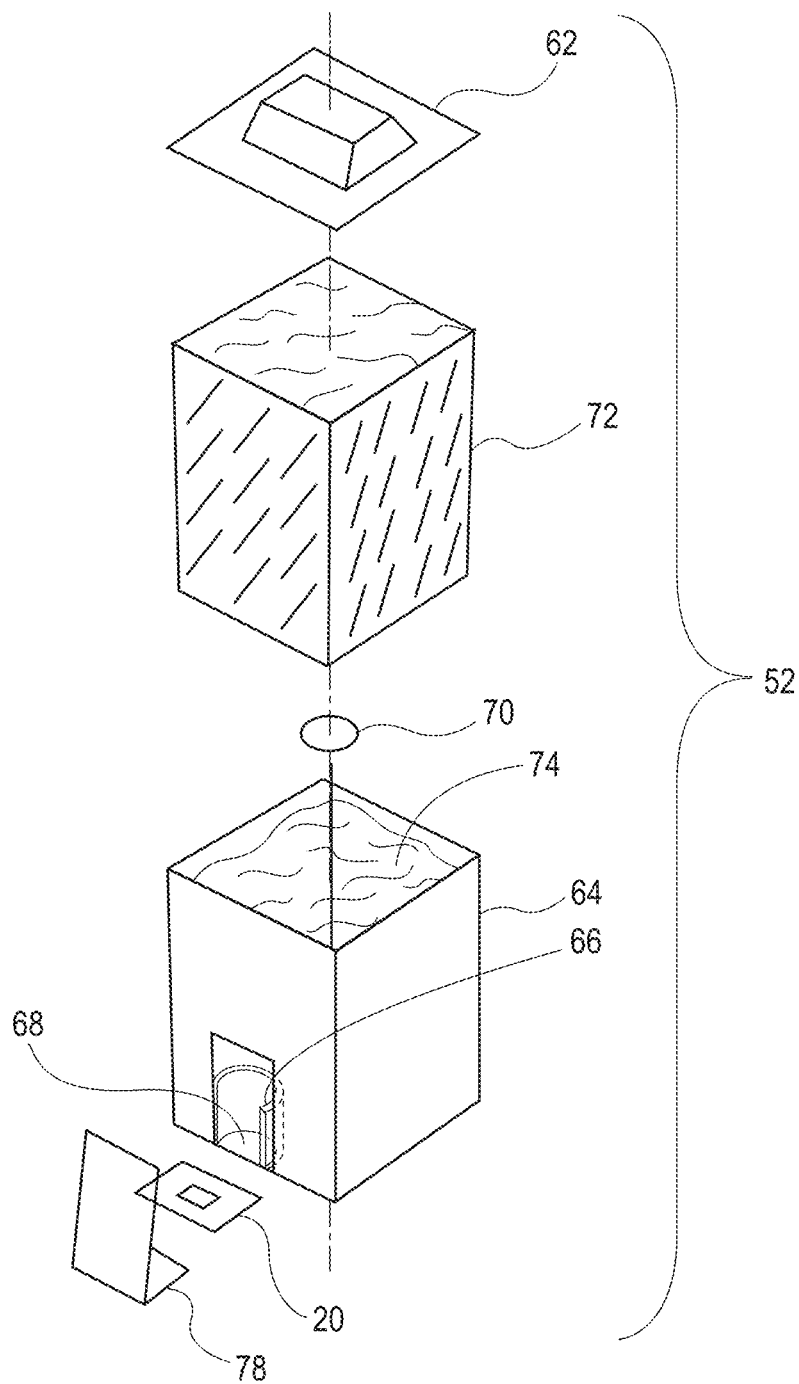
FIG. 3 is a cartridge useful in the present invention.

Turning now to FIG. 3, which is an exploded view of the cartridge 52 comprising cartridge cap 62 and cartridge body 64. Cartridge body 64 includes standpipe 66 which is typically enclosed within cartridge body 64 and defines nozzle outlet 68. Optional filter 70 helps keep excessively large particles, and other debris out of the nozzle array 20. Filter 70 and nozzle array 20 are on opposite sides of nozzle outlet 68. Pigmented cosmetic composition 74 partially fills cartridge body 64. Foam core 72 fills cartridge 64 and helps to regulate back pressure of pigmented cosmetic composition 74. Back pressure can be regulated via bladders (not shown) and other methods known to the art, the foam core shown here is just one example of how to help regulate flow of the pigmented cosmetic composition 74 to standpipe 66 through filter 70 and into nozzle array 20. Connector 78 provides the electrical power and signal to nozzle array 20. Pigmented cosmetic composition 74 may be ejected from the cartridge 52 by piezoelectric means, thermal means, mechanical pumping means, or a combination of these.

Figure 4:
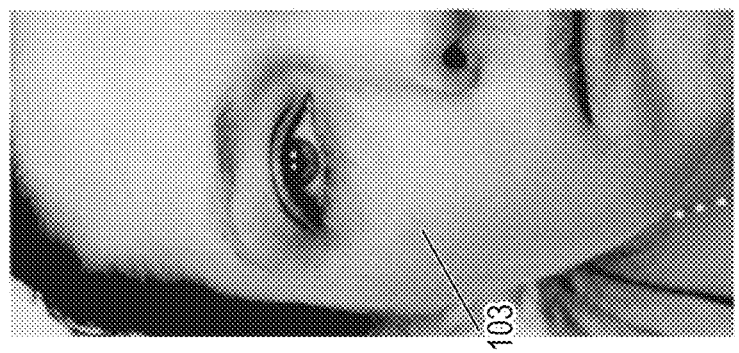
FIG. 4 is the natural, uncovered skin of a female user.
Figure 5:
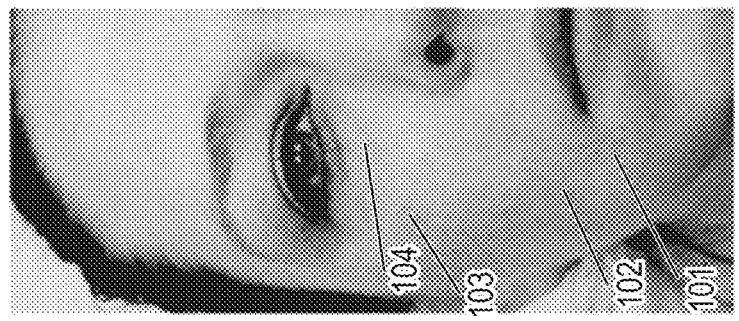
FIG. 5 is the same female user in FIG. 4 with applied makeup.
Figure 6:
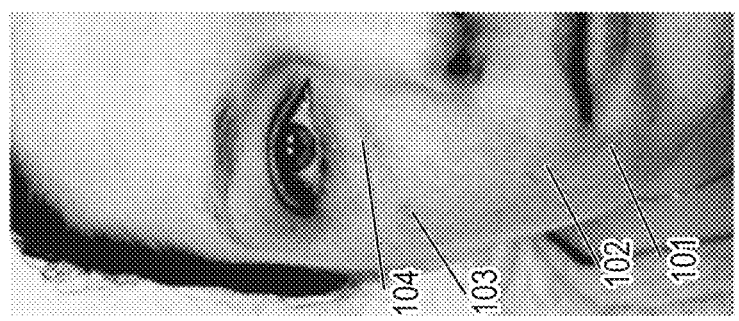
FIG. 6 is the same female user as shown in FIG. 4, with no makeup on, after using the deposition device useful in the present invention.

Referring now to FIGS. 4, 5, and 6, which are photographs of the same female subject. FIG. 4 represents the subject's washed, natural, and uncoated skin. FIG. 5 was taken after the subject applied makeup to her face in a manner she would normally do. FIG. 6 was taken after the subject's makeup was removed and her face treated with the deposition device of this invention. FIGS. 4, 5, and 6 are all taken on the same day, with no appreciable sun exposure between photographs (i.e. the subject was indoors for the entire modification period).

Tonal imperfections 101, 102, 103 and 104 are clear in FIG. 4. After makeup is applied, tonal imperfections 101, 102, 103 and 104 are all still visible as shown in FIG. 5. FIGS. 4 and 5 show that makeup changes the overall tone of human skin, but does not cover up the tonal imperfections.

The subject washed her face to remove the applied makeup after the photograph of FIG. 5 was taken. The subjects skin is then modified with the deposition device of this invention and the photograph of FIG. 6 was taken. Tonal imperfections 101, 102 and 104 from FIGS. 4 and 5 are largely invisible in FIG. 6. Tonal imperfection 103 is barely visible after modification with the deposition device useful in the present invention. The deposition device provides a substantial and visible change to the appearance of human skin versus the natural condition of the skin and the skin with applied makeup.

The background L can be calculated anywhere within the image. The image is taken where the nozzles will fire the pigmented cosmetic composition. The background L can be the arithmetic average, median, or mean of a plurality of local Ls, which means the calculation can include all of the local Ls in the image, or a subset thereof.

The predetermined $\Delta L_S$ is the absolute value of the difference between the local L and the background L. This value, $\Delta L_S$, can be defined in absolute numbers or as a percentage. The sensor is for example a camera that takes black and white or color images, a spectrophotometer, or similar devices that are sensitive to electromagnetic energy wavelengths. The images are taken, or converted to a standard grey scale that is known to the art. It is understood that any numerical scale that measures lightness to darkness can be considered a "grey scale". Moreover, as used herein, "grey scale" is intended to be a linear scale, or one band, or one visual attribute. For example, one "grey scale" visual attribute could be single wavelength or a narrow wavelength to define a specific visual color. Another example of one "grey scale" visual attribute could be a mix of wavelength numerical values averaged for each pixel making up the image, such as a true black, grey or white image from an RGB mixture.

It will also be understood to those skilled in the art that the background L value should not be too close to the ends of this scale. For example, if the grey scale is 0-100, with 0 being pure black and 100 being pure white, a background in the 0-10 range, or in the 90-100 range may be too light or too dark to show meaningful differences. Accordingly, one can adjust the background lighting, or the gain on the sensor taking the image, to move the background L closer to the middle of the scale. In this example, a background L of 50 would be ideal, with a background L in the range of 10-90 preferred, 20-80 even more preferred.

The most common grey scale is 0-255 (no units) and other examples include 0-1024 and 0-4096. For a grey scale of 0-255, the difference between grey scale steps is at least 1/255. In this example, it would be desirable to use sensor and lighting settings that provide a background L value between 60 and 210. Using the 0-255 gray scale, the $\Delta L_S$ is preferably at least 0.5, more preferably at least 1, and even more preferably at least 1.5, to initiate modification of the skin surface. Likewise, $\Delta L_S$ can be measured as a percentage, for example, a numerical $\Delta L_S$ of 2.6 is approximately equal to 1.0% of a 255 grey scale. Thus, $\Delta L_S$ may be plus or minus 0.25%, preferably plus or minus 0.5%, even more preferably plus or minus 0.75%, of the grayscale.

There is no technical difference between an image used for background L values and those used for local L values, the difference is in the analysis of the image. Hence, the images are continually sent to the processor to calculate the L values and $\Delta L_M$ values. By "sent" it is understood, that preferably at least 4 bits of data per pixel are transferred for each image, and preferably, this 4-bit (or more) packet of data is used in the calculation of each local L value.

It is understood, that the background L can be calculated once in a treatment period and that value can be reused throughout the treatment period. Alternatively, it can be continually recalculated as long as the treatment process goes on. Moreover, there can be pre-programmed triggers to initiate a recalculation of the background L. Also, the background L may be retrieved from the processor memory to be used for the current background L. For example, if an extended period of time elapses and no tonal imperfections are found, or if tonal imperfections are being found too frequently, a new background L might automatically be calculated. Likewise, $\Delta L_S$ can be a set value that remains constant throughout the treatment cycle or it too can vary. $\Delta L_S$ can be reset during the treatment cycle for any of a variety of reasons. If too many nozzles are firing too frequently, the $\Delta L_S$ can be adjusted to lower the intensity of the nozzle firing. Similarly, if the nozzles are firing too infrequently, $\Delta L_S$ can be adjusted in the opposite direction to increase the sensitivity of tonal imperfection detection.

Those skilled in the art will appreciate that modifying $\Delta L_S$ during modification is a matter of programming the processor to or with a desired algorithm.

When the $\Delta L_M$ exceeds the predetermined value, the tonal imperfection is treated with the pigmented cosmetic composition. Treatment requires firing one or more of the nozzles which dispense the pigmented cosmetic composition onto the skin surface in the area of the tonal imperfection.

More specifically, the pigmented cosmetic composition is applied via an array of nozzles and the local L is calculated along the length of, and in the firing range of, the array of nozzles. The "firing range" of a nozzle will vary based on its size, type, the speed the device is moving, distance from the target, and other parameters. Examples of various types of nozzles suitable for use in the present devices are given below. In general, "near the nozzle" as used herein is meant to mean the image taken to calculate a local L value is close to the area of skin surface where the pigmented cosmetic composition is deposited by the nozzle (the firing range, or landing zone of the nozzle). Without intending to limit the invention, near the nozzle means the image should be taken within a radius of about 2 cm, preferably about 1 cm, and even more preferably about 0.7 cm from the center of the nozzle.

An individual nozzle may be fired to deposit the pigmented cosmetic composition, or multiple nozzles can be fired at the same time. The number of nozzles fired along the array of nozzles can be adjusted based on the size of the $\Delta L_M$ and the size of the tonal imperfection. Furthermore, the frequency of nozzle firing can be adjusted based on the $\Delta L_M$, with more droplets being fired in succession in response to larger $\Delta L_M$ values.

Firing intensity curves can be programmed into the processor to adjust the firing rate of nozzles. For example, if $\Delta L_M$ is equal to or slightly greater than $\Delta L_S$, then the adjacent nozzle is fired 1 time. If $\Delta L_M$ increases to $2*\Delta L_S$, then the adjacent nozzle is fired 25 times. If the $\Delta L_M$ is $3*\Delta L_S$, then the adjacent nozzle is fired 100 times. This non-limiting example is intended to show how the size of the $\Delta L_M$ with respect to the $\Delta L_S$ can determine the amount, and hence, the intensity of the firing of the nozzles adjacent the tonal imperfection. Those skilled in the art will appreciate that plotting a firing intensity curve using 2, 3, or more data points, and then programming that firing intensity curve into the processor are known techniques.

While inkjet cartridges are shown and exemplified herein, pigmented cosmetic compositions may be applied with other "flow control" devices or non-drop control devices. Flow control devices typically are characterized as "drop control techniques" where individual droplets of the substance are controlled. Ink jet printers, which are known to the art, are examples of drop on demand applicators and this technology is applicable for use in the present invention. Piezo electric drop control devices and other micro electromechanical systems are appropriate for use with the current deposition device. Spray devices and electrostatic spray devices are non-drop control techniques where droplets are produced and controlled only in aggregate. Often in a spray device, a lack of individual droplet control, or "randomness" is desired in order to produce a smooth application over a relatively large area. By contrast, it is often desirable to provide very specific control of the amount and placement of the compositions.

Examples of drop control can include "fine flow control" where the flow of the substance is precisely controlled to deliver droplets as desired and "inkjet technologies." An older inkjet technology includes supplying a continuous flow of charged droplets past electrostatic deflector plates which are alternately charged so that the plates either permit a droplet to pass or deflect to a gutter. Other inkjet technologies include "drop on demand" such as thermal devices provided by Hewlett Packard, and piezoelectric devices such as provided by Epson and other printer manufacturers. In one embodiment of the current invention, a drop on demand technology is combined with charging the droplets.

The deposition device useful in the present invention is preferably handheld but can be tethered to a structure that moves the deposition device across the skin surface to be modified. If handheld, the user can simply move the deposition device across the skin surface to be modified. Optionally, multiple deposition devices can be configured in a stationary structure wherein the user places the skin surface to be modified and multiple readings and applications occur simultaneously or in sequence.

The pigmented cosmetic composition can be applied to the skin surface by scanning and applying at the same time while making multiple passes over the surface. Several advantages result from using multiple pass application. The process for multiple pass applications is to make a partial application of the pigmented cosmetic composition, then to scan again the area of skin surface that has received the partial application. A further application of pigmented cosmetic compositions can be made, and still further multiple pass scanning and applications can be made to approach an aesthetic goal. Thus, the user can select the end point of the modification, i.e. the "aesthetic goal", thus tailoring the modification time to individual needs and preferences. Attempting to make all corrections in one pass has been shown to overcorrect in certain areas.

In one aspect, the pigmented cosmetic composition is deposited onto about 1% to about 40% of the surface area of the user's skin for the skin regions that the device has been exposed to, alternatively less than about 20%, alternatively less than about 10%, alternatively less than about 5%, alternatively less than about 1%, alternatively less than about 0.5%. This can be desirable because it can provide a reduced tactile impact as more of the user's basal skin is exposed and not covered by the pigmented cosmetic composition.

Inkjet devices, whether piezo or thermal, can generate droplets in the range of about 1 picoliter to more than 100 picoliters depending on the application. In the current system, it is desirable for the droplet size to be small enough to not be visible when deposited onto the skin, even when observed from close distances. Without being limited by theory, it is believed that the largest discreet droplets that remain invisible to the naked eye when on the skin are approximately 60-100 microns in diameter depending on the distance and visual acuity of the person observing the droplet. The droplet volume of product varies depending on the fluidic properties which include viscosity, surface energy, vapor pressure, etc. However, based on droplet geometry it is reasonable to assume that the maximum individual drop volume that can create surface spot sizes less than 60 microns in diameter is approximately 100 picoliters.

The deposition device may apply the pigmented cosmetic composition in droplets having an average diameter of from about from about 0.1 μm to about 60 μm, alternatively from about 1 μm to about 50 μm, alternatively from about 5 μm to about 40 μm. Preferably, the pigmented cosmetic composition can be applied to the tonal imperfection in a discontinuous pattern of discrete droplets.

Pigmented Cosmetic Composition

The pigmented cosmetic composition can hide or camouflage a tonal imperfection, such as hyperpigmentation, when deposited precisely and substantially only onto the tonal imperfection.

The pigmented cosmetic composition can comprise particles. In one aspect, pigmented cosmetic composition preferably comprises a particle settling rate of less than 0.06 mm per day at 25° C. and 1 atm pressure. The pigmented cosmetic composition may further have an elastic modulus between about 0.1 Pa to about 1000 Pa at 25 C and 1000 Hz. Solid wax based pigmented cosmetic compositions may have an elastic modulus of up to about 100 MPa. Preferably, the particles in the pigmented cosmetic composition have a refractive index of between about 1.1 and about 5.0.

In one aspect, the pigmented cosmetic composition can comprise an opacity of at least 0.2. In one aspect, the pigmented cosmetic composition can comprise an opacity of from about 0.2 to about 1, alternatively from about 0.25 to about 0.8, alternatively from about 0.3 to about 0.5.

The pigmented cosmetic composition can comprise inks, dyes, pigments, adhesives, curable compositions, optically activated compounds, metal oxides such as iron, zinc, or titanium oxides, bleaching agents, texture reducing polymers, cosmetics, hair colorants, and combinations thereof. In one aspect, the pigmented cosmetic composition can comprise metal oxides comprising an average particle size of greater than 100 nm.

In one aspect, the pigmented cosmetic composition can be a skin care composition, hair care composition, hair removal composition (often referred to as depilatories), hair growth stimulant, and mixtures thereof.

The pigmented cosmetic compositions can be delivered alone or in the presence of a dermatologically-acceptable carrier. The phrase "dermatologically-acceptable carrier", as used herein, means that the carrier is suitable for topical application to the skin tissue, has good aesthetic properties, is compatible with any additional components of the pigmented cosmetic composition, and will not cause any untoward safety or toxicity concerns. The carrier can be in a wide variety of forms. Non-limiting examples include simple solutions (water or oil based), emulsions, and solid forms (gels, sticks, flowable solids, amorphous materials). In certain embodiments, the dermatologically acceptable carrier is in the form of an emulsion. Emulsions may be generally classified as having a continuous aqueous phase (e.g., oil-in-water and water-in-oil-in-water) or a continuous oil phase (e.g., water-in-oil and oil-in-water-in-oil). The oil phase may comprise silicone oils, non-silicone oils such as hydrocarbon oils, esters, ethers, and the like, and mixtures thereof. Emulsion carriers can include, but are not limited to, continuous water phase emulsions such as silicone-in-water, oil-in-water, and water-in-oil-in-water emulsions; continuous oil phase emulsions such as water-in-oil and water-in-silicone emulsions; and oil-in-water-in-silicone emulsions.

In one aspect, the pigmented cosmetic composition can be oil-free.

The pigmented cosmetic composition can be delivered in a variety of product forms including, but not limited to, a cream, a lotion, a gel, a foam, a paste, or a serum. Additionally, the pigmented cosmetic composition can include for purposes of proper formulation and stabilization anti-fungal and anti-bacterial components.

The pigmented cosmetic composition can comprise a humectant as a carrier or chassis for the other components in the pigmented cosmetic composition. An exemplary class of humectants include polyhydric alcohols. Suitable polyhydric alcohols include polyalkylene glycols and alkylene polyols and their derivatives, including propylene glycol, dipropylene glycol, polypropylene glycol, polyethylene glycol and derivatives thereof; sorbitol; hydroxypropyl sorbitol; erythritol; threitol; pentaerythritol; xylitol; glucitol; mannitol; butylene glycol (e.g., 1,3-butylene glycol); pentylene glycol; hexane triol (e.g., 1,2,6-hexanetriol); glycerin; ethoxylated glycerine; and propoxylated glycerine. Other suitable humectants can include sodium 2-pyrrolidone-5-carboxylate; guanidine; glycolic acid and glycolate salts (e.g., ammonium and quaternary alkyl ammonium); lactic acid and lactate salts (e.g., ammonium and quaternary alkyl ammonium); aloe vera in any of its variety of forms (e.g., aloe vera gel); hyaluronic acid and derivatives thereof (e.g., salt derivatives such as sodium hyaluronate); lactamide monoethanolamine; acetamide monoethanolamine; urea; sodium pyroglutamate, water-soluble glyceryl poly(meth) acrylate lubricants (such as Hispagel®); and mixtures thereof.

Colorants can be used to modify the color or reflectance of the skin surface. Compositions comprising colorants are commonly used to modify color and reflectance in cosmetic make-up compositions. Foundation, lipstick, eyeliner are just a few examples of these make-up compositions, but they are all applied evenly across large portions of the skin surface, that is they are macro-applications. In sharp contrast, the present pigmented cosmetic compositions are selectively applied on a very small scale to select areas, that is they are intended for a micro application. Suitable colorants for use in the pigmented cosmetic composition can include inorganic or organic pigments and powders. Organic pigments can include natural colorants and synthetic monomeric and polymeric colorants. Organic pigments include various aromatic types such as azo, indigoid, triphenylmethane, anthraquinone, and xanthine dyes which are designated as D&C and FD&C blues, browns, greens, oranges, reds, yellows, etc. Organic pigments may consist of insoluble metallic salts of certified color additives, referred to as the Lakes. Inorganic pigments include iron oxides, ferric ammonium ferrocyanide, manganese violet, ultramarines, chromium, chromium hydroxide colors, and mixtures thereof. The pigments may be coated with one or more ingredients that cause the pigments to be hydrophobic. Suitable coating materials that will render the pigments more lipophilic in nature include silicones, lecithin, amino acids, phospholipids, inorganic and organic oils, polyethylene, and other polymeric materials. Suitable silicone treated pigments as disclosed in U.S. Pat. No. 5,143,722. Inorganic white or uncolored pigments include $TiO_2$, $ZnO$, or $ZrO_2$, which are commercially available from a number of sources. Other suitable colorants are identified in U.S. Pat. No. 7,166,279. Colorants are generally included at a weight percent such that the pigmented cosmetic composition yields a perceptible color. The colorant particle shape is typically spherical, polygonal or fractal. In one embodiment, the pigmented cosmetic composition exhibits a color that perceptibly different from the color of the applicator. By perceptibly different, refers to a difference in color that is perceptible to a person having normal sensory abilities under standard lighting conditions (e.g., natural illumination as experienced outdoors during daylight hours, the illumination of a standard 100 watt incandescent white light bulb at a distance of 2 meters, or as defined by CIE D65 standard illuminate lighting at 800 lux to a 1964 CIE standard observer).

The pigmented cosmetic composition can comprise an adhesive that is compatible with skin surfaces. Commercially available adhesives compatible with skin surfaces are available from the 3M Corporation of Minneapolis Minn. See, for example: U.S. Pat. No. 6,461,467, issued to Blatchford, et al.; U.S. Pat. No. 5,614,310, issued to Delgado, et al.; and U.S. Pat. No. 5,160,315, issued to Heinecke et al., incorporated herein by reference. In one aspect, a pigmented cosmetic composition comprising an adhesive can be selectively applied to the skin surface and a second pigmented cosmetic composition can be dusted on the skin surface where can will stick to the adhesive. The second pigmented cosmetic composition that is not adhered to the skin surface can then be removed leaving behind a selective, micro application of the second pigmented cosmetic composition.

Likewise, the pigmented cosmetic composition can comprise curable compositions that cure upon exposure to certain wavelengths of energy, infrared light for example. In one aspect, a pigmented cosmetic composition comprising a curable composition can be selectively applied to the skin surface and can be cured by exposing the skin surface to the curing energy source. The entire skin surface can be exposed, or the exposure can be done at the same time as the application.

The pigmented cosmetic composition can be an anti-wrinkle composition comprising a tensioning polymer and/or film-forming polymers. Suitable tensioning polymers are described in US Patent Applications US20060210513A1, filed by Luizzi, et al. and suitable film-forming polymers are described in US20070148120A1, filed by Omura et al., incorporated herein by reference.

The pigmented cosmetic composition can comprise optically-activated particles. Sometimes referred to as "interference pigments", these optically-activated particles include a plurality of substrate particles selected from the group consisting of nylons, acrylics, polyesters, other plastic polymers, natural materials, regenerated cellulose, metals and minerals; an optical brightener chemically bonded to each of the plurality of substrate particles to form integral units in the form of optically-activated particles for diffusing light. These particles can help to reduce the visual perception of tonal imperfections, including cellulite, shadows, skin discolorations, and wrinkles. Each of the optically-activated particles are encapsulated with a UV transparent coating to increase the diffusion light to further reduce the visual perception of the tonal imperfections. The encapsulated optically-activated particles are able to absorb ultraviolet radiation and emit visible light; and the encapsulated optically-activated particles are able to both scatter and absorb light in a diffuse manner in order to reduce the visual perception of tonal imperfections, including cellulite, wrinkles, shadows, and skin discolorations, when the optically-activated particles are applied to the skin surface.

The pigmented cosmetic composition can be a skin care composition such as a moisturizer, a conditioner, an anti-aging composition, a skin lightening composition, a sunscreen, a sunless tanner, and combinations thereof.

The pigmented cosmetic composition may comprise a safe and effective amount of one or more actives useful for regulating and/or improving skin condition. "Safe and effective amount" means an amount of a compound or composition sufficient to induce a positive benefit but low enough to avoid serious side effects (i.e., provides a reasonable benefit to risk ratio within the judgment of a skilled artisan). A safe and effective amount of an active can be from about $1 \times 10^{-6}$ to about 25% by weight of the total composition, alternatively from about 0.0001 to about 25% by weight of the total composition, alternatively from about 0.01 to about 10% by weight of the total composition, alternatively from about 0.1 to about 5% by weight of the total composition, alternatively from about 0.2 to about 2% by weight of the total composition.

Suitable actives include, but are not limited to, vitamins (e.g., B3 compounds such as niacinamide, niacinnicotinic acid, tocopheryl nicotinate; B5 compounds, such as panthenol; vitamin A compounds and natural and/or synthetic analogs of Vitamin A, including retinoids, retinol, retinyl acetate, retinyl palmitate, retinoic acid, retinaldehyde, retinyl propionate, carotenoids (pro-vitamin A); vitamin E compounds, or tocopherol, including tocopherol sorbate, tocopherol acetate; vitamin C compounds, including ascorbate, ascorbyl esters of fatty acids, and ascorbic acid derivatives such as magnesium ascorbyl phosphate and sodium ascorbyl phosphate, ascorbyl glucoside, and ascorbyl sorbate), peptides (e.g., peptides containing ten or fewer amino acids, their derivatives, isomers, and complexes with other species such as metal ions), sugar amines (e.g., N-acetyl-glucosamine), sunscreens, oil control agents, tanning actives, anti-acne actives, desquamation actives, anti-cellulite actives, chelating agents, skin lightening agents, flavonoids, protease inhibitors (e.g., hexamidine and derivatives), non-vitamin antioxidants and radical scavengers, peptides, salicylic acid, hair growth regulators, anti-wrinkle actives, anti-atrophy actives, minerals, phytosterols and/or plant hormones, tyrosinase inhibitors, N-acyl amino acid compounds, moisturizers, plant extracts, and derivatives of any of the aforementioned actives. The term "derivative" as used herein refers to structures which are not shown but which one skilled in the art would understand are variations of the basic compound. For example, removing a hydrogen atom from benzene and replacing it with a methyl group. Suitable actives are further described in U.S. application publication No. US2006/0275237A1 and US2004/0175347A1, incorporated herein by reference.

Consumer Test

A consumer test was conducted to evaluate the ability of four shades of pigmented cosmetic composition to camouflage tonal imperfections across a range of consumer skin tones. The four shades evaluated were light, medium, medium-dark, and dark and correspond to Samples A-D, respectively.

Panelists were selected using the following criteria:
Skin condition: hyperpigmentation
Skin tone: Fitzpatrick Scale Type I-VI
All participants were female, age 25-65
No open sores or active acne
No participants had been to a dermatologist or esthetician for any skin lightening procedures 41 panelists used 2 samples selected based on their Fitzpatrick Scale Type. The number of panelists for each Fitzpatrick Scale Type are as follows: Type I and II: 6; Type III: 6; Type IV: 16; and Type V and VI: 13.

Images of the right and left side of each panelist were taken at baseline (bare, clean skin). The L*C*h* values for each panelist's face were obtained using the LCh Test Method for Skin as described hereinafter. The panelist identified her own skin tone and the corresponding sample was selected. The sample was applied to one half of the panelist's face by the study coordinator using the deposition device of described above. After application of the sample, each panelist filled out a questionnaire to assess the acceptance of the end look and a second "after" image was taken. The ratings were on a 100-point scale as follows: (100) excellent, (75) very good, (50) good, (25) fair, and (0) poor. The same was repeated for the other side of the panelist's face with a different sample selected by the study coordinator that corresponded to the panelist's skin tone as determined by the study coordinator. The rating for each sample applied to the panelist was compared and a preferred shade was selected. The data for the preferred shade was combined and reported in Table 1 below. If there was no preference for a shade, the data from those panelists was excluded from the table.

Images were captured using a Canfield Visia System with setting the following settings parameters—Lighting: Standard 2, CR2; Detection Threshold: 6; Minimum Spot Diameter: 1.3 mm; Maximum Spot Diameter: 50 mm; Masking: Cheek Only.

Table 1 below summarizes the results of the Consumer Test. The ΔL* is calculated as the difference in the average L* of the sample−average L* of the skin. The ΔC* is calculated as the difference in the average C* of the sample−average C* of the skin. Visible spot reduction is calculated by taking the difference in the spot area of the "baseline" image and the "after" image. Visible spot analysis provides quantitative data and scoring for spots visible under standard daylight conditions. Visible spot reduction is reported as the % visible spot. The overall sample rating is reported as the average score from the panelists who graded each sample.

Samples A-D evaluated by the panelists correspond to Examples 1-4, respectively, described hereinafter.

TABLE 1

| Sample | n | Avg. Skin L* Value | Avg. Skin C* Value | Avg. Skin h* Value | ΔL* | ΔC* | % Visible Spot | Overall Sample Rating |
|---|---|---|---|---|---|---|---|---|
| A | 8 | 62.9 | 19.9 | 60.4 | 20.6 | 4.6 | −52.0 | 78.1 |
| B | 11 | 59.7 | 21.8 | 60.3 | 23.3 | 9.1 | −57.2 | 88.6 |
| C | 10 | 54.8 | 22.3 | 60.5 | 22.9 | 14.2 | −42.6 | 85.0 |
| D | 4 | 38.8 | 19.1 | 57.0 | 31.1 | 18.1 | −48.4 | 75.0 |

It was surprisingly found that as the average skin L* value decreased the average delta C* of the cosmetic composition needed to increase. It was found that panelists with a lighter skin tone, for instance having a self-assessed Fitzpatrick Scale Type II-IV, preferred a sample with a delta C* value of 0 to 14, while panelists with a darker skin tone, for instance a self-assessed Fitzpatrick Scale Type V-VI, preferred a sample with a delta C* value of 8 to 21. It was also found that the delta L* between the sample and the skin ranged from 20 to 31. Finally, all four samples resulted in a greater than 40% reduction in visible spots and all samples were rated by the panelists as very good or excellent.

In the same consumer test, a separate group of panelists were purposely given one sample with a shade outside of the preferred ranges. In each case, the "incorrect" shade was rated by the panelist as not preferred. This data is summarized in Table 2 below.

TABLE 2

| Panelist | Sample | Avg. Skin L* Value | Avg. Skin C* Value | Avg. Skin h* Value | ΔL* | ΔC* | % Visible Spot | Overall Sample Rating |
|---|---|---|---|---|---|---|---|---|
| 1 | D | 65.3 | 21.1 | 63.6 | 4.7 | 16.1 | +53.4 | 0.0 |
| 2 | D | 62.3 | 20.5 | 56.9 | 7.7 | 16.7 | +10.5 | 0.0 |
| 3 | D | 55.6 | 22.5 | 57.6 | 14.4 | 14.7 | −43.9 | 50.0 |

Panelists 1-3 each received Sample D on one side of her face. Panelists 1 and 2 had an average skin L* value less than ten units lower than L* value of Sample D. In both cases, each panelist rated the acceptance of the end look as "poor" (0) because the spots on her face were not able to be lightened enough to match the L* of the surrounding skin. Panelist 3 had an average skin L* value of about 55 and the delta L* between the sample and her skin was 14.4, which falls within the acceptable ranges. However, the panelist rated the acceptance of the end look as only "good" (50) because Sample D had too much chroma for her skin tone.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

The following 4 Examples are pigmented cosmetic compositions of the present inventions. They can be applied by any of the methods and devices described herein, preferably, they are applied via a thermal ink jet printer head and cartridge combination. Dispersions were supplied by KOBO Products, Inc (South Plainfield, N.J.). PuraGuard™ Propylene Glycol was obtained from Dow Chemical Company (Lake Zurich, Ill.). Symdiol® 68 was obtained from Symrise AG (Branchburg, N.J.). Darvan® 811D was obtained from Vanderbilt Minerals, LLC (Norwalk, Conn.). Sepiwhite was obtained from Seppic (Paris, France).

Example 1

| Phase | Ingredient | Description | % W/W (as added) |
|---|---|---|---|
| A | WPG75PFSP | 75% TiO2 Slurry in Propylene Glycol/Water | 22.88 |
| A | WPG45GYSP | 45% Iron Oxide Slurry Propylene Glycol/Water | 2.74 |
| B | Water | Deionized Water | 35.66 |
| B | Propylene Glycol | Propylene Glycol | 22.50 |
| B | Symdiol ® 68 | Hexanediol/Caprylyl Glycol | 1.00 |

-continued

| Phase | Ingredient | Description | % W/W (as added) |
|---|---|---|---|
| B | Darvan ® 811D | 5% Sodium Polyacrylate in water | 1.00 |
| C | WPG45SIRSP | 45% Iron Oxide Slurry Propylene Glycol/Water | 0.22 |
| D | Water | Deionized Water | 10 |
| E | Sepiwhite | 5% Undecylenoyl Phenylalanine in water | 4.00 |
| | | Total | 100.00 |

Example 2

| Phase | Ingredient | Description | % W/W (as added) |
|---|---|---|---|
| A | WPG75PFSP | 75% TiO2 Slurry in Propylene Glycol/Water | 21.56 |
| A | WPG45GYSP | 45% Iron Oxide Slurry Propylene Glycol/Water | 6.20 |
| B | Water | Deionized Water | 34.16 |
| B | Propylene Glycol | Propylene Glycol | 21.99 |
| B | Symdiol ® 68 | Hexanediol/Caprylyl Glycol | 1.00 |
| B | Darvan ® 811D | 5% Sodium Polyacrylate in water | 1.00 |
| C | WPG45SIRSP | 45% Iron Oxide Slurry Propylene Glycol/Water | 0.09 |
| D | Water | Deionized Water | 10.00 |
| E | Sepiwhite | 5% Undecylenoyl Phenylalanine in water | 4.00 |
| | | Total | 100.00 |

Example 3

| Phase | Ingredient | Description | % W/W (as added) |
|---|---|---|---|
| A | WPG75PFSP | 75% TiO2 Slurry in Propylene Glycol/Water | 17.19 |
| A | WPG45GYSP | 45% Iron Oxide Slurry Propylene Glycol/Water | 11.98 |
| B | Water | Deionized Water | 33.61 |
| B | Propylene Glycol | Propylene Glycol | 20.75 |
| B | Symdiol ® 68 | Hexanediol/Caprylyl Glycol | 1.00 |
| B | Darvan ® 811D | 5% Sodium Polyacrylate in water | 1.00 |
| C | WPG45SIRSP | 45% Iron Oxide Slurry Propylene Glycol/Water | 0.47 |
| D | Water | Deionized Water | 10.00 |
| E | Sepiwhite | 5% Undecylenoyl Phenylalanine in water | 4.00 |
| | | Total | 100.00 |

Example 4

| Phase | Ingredient | Description | % W/W (as added) |
|---|---|---|---|
| A | WPG75PFSP | 75% TiO2 Slurry in Propylene Glycol/Water | 14.47 |
| A | WPG45GYSP | 45% Iron Oxide Slurry Propylene Glycol/Water | 14.75 |
| B | Water | Deionized Water | 32.63 |
| B | Propylene Glycol | Propylene Glycol | 19.90 |
| B | Symdiol ® 68 | Hexanediol/Caprylyl Glycol | 1.00 |
| B | Darvan ® 811D | 5% Sodium Polyacrylate in water | 1.00 |
| C | WPG45SIRSP | 45% Iron Oxide Slurry Propylene Glycol/Water | 2.25 |
| D | Water | Deionized Water | 10.00 |
| E | Sepiwhite | 5% Undecylenoyl Phenylalanine in water | 4.00 |
| | | Total | 100.00 |

Examples 1-4 can be made according to the following procedure. First, the ingredients of Phase A are combined in an appropriate premix container. The ingredients of Phase B are added into a main container. Phase B is milled using a dispersing instrument at low speed until the mixture is homogenous. A suitable dispersing instrument is a digital ULTRA-TURRAX® available from IKA® (Staufen im Breisgau, Germany). Phase C is then added to the main container while continuing to mill. While milling, Phase A is added into the main container. Then, the premix container is washed with Phase D and then poured into the main container. The main container is mixed for 30 min. After mixing, the milling speed is lowered and Phase E is added. Homogeneity is ensured and then the mixture is poured into a container, labeled, and stored at ambient conditions.

LCh Test Method for a Composition

The L*C*h* values of a sample composition can be measured according to the ASTM method D5326-94a, standard test method for color development in tinted latex paint (Jul. 1, 2013). A color spectrophotometer (such as a Datacolor Check II® available from Datacolor, Lucerne, Switzerland, or an equivalent) is used to take a measurement under the following conditions: Illuminant D65/10, Data CIELCh, Large Area View (LAV) 15 mm aperture. The color spectrophotometer is calibrated according to the manufacturer instructions. Then a reading is taken of the cuvette filled with the sample composition and the L*C*h* values are recorded. Two readings are taken for each sample, and the average L*C*h* values of the two readings is reported.

LCh Test Method for Skin

The L*C*h* values of skin is measured according to the ASTM method D2244-16 (Jul. 1, 2016), Standard Practice for Calculation of Color Tolerances and Color Differences from Instrumentally Measured Color Coordinates. The skin of a user is cleaned and dried such that it is substantially free of cosmetics and/or any other compositions. A color spectrophotometer (such as a Datacolor Check II® available from Datacolor Lucerne, Switzerland, or an equivalent) is used to take measurements of the user's skin under the following conditions: Illuminant D65/10, Data CIELCh, LAV 15 mm aperture. The spectrophotometer is calibrated according to manufacturer instructions. Then a reading is taken of the user's left cheek and the L*C*h* values are recorded. Three readings are taken for each user in three different areas of the cheek and the average L*C*h* values of the three readings is reported.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An array of cosmetic compositions intended to camouflage imperfections on human skin in a targeted manner comprising:
   a. from about two to about ten different shades of cosmetic compositions, wherein each shade of cosmetic composition comprises a metal oxide selected from the group consisting of zinc oxide, iron oxide, titanium oxide and mixtures thereof;
   b. wherein said different cosmetic compositions each have an L* value, wherein the L* value for each of said cosmetic compositions is within the range of from about 60 to about 90;
   c. wherein one or more of the cosmetic compositions from the array will effectively camouflage imperfections on a consumer's skin if said consumer has an average skin L* value between about 35 and about 75;
   d. wherein the cosmetic composition(s) that effectively camouflages the imperfections on a consumer's skin comprises an average composition L* value of about 10 to about 40 units greater than an average skin L* value of the user; and
   e. wherein said different cosmetic compositions each have a C* value, wherein the C* value for each of said cosmetic compositions is within the range of from about 15 to about 45.

2. The array of claim 1 wherein the L* value for each of said cosmetic compositions is within the range of from about 65 to about 85.

3. The array of claim 1 wherein the L* value for each of said cosmetic compositions is within the range of from about 65 to about 85, and wherein one or more of the cosmetic compositions from the array will effectively camouflage imperfections on a consumer's skin if said consumer has an average skin L* value between 35 and 75.

4. The array of claim 1 wherein said two or more different cosmetic compositions each have an opacity of at least 0.2.

5. The array of claim 1 wherein said two or more different cosmetic compositions each have an opacity of from about 0.2 to about 1.

6. The array of claim 1 wherein said two or more different cosmetic compositions each have an opacity of 0.25 to about 1.0.

7. The array of claim 1 wherein said two or more different cosmetic compositions each have an opacity of 0.3 to about 1.0.

8. The array of claim 1 wherein said two or more different cosmetic compositions each have a C* value, wherein the C* value for each of said cosmetic compositions is within the range of from about 20 to about 40.

9. The array of claim 1 wherein said two or more different cosmetic compositions each have an h* value, wherein the h* value for each of said cosmetic compositions is within the range of about 50 to about 80.

10. The array of claim 1 wherein said metal oxide has a particle size from about 100 nm to about 50 microns.

11. The array of claim 1 wherein said metal oxide has a particle size from about 200 nm to about 10 microns.

12. The array of claim 1 wherein said array comprises from about three to about seven different cosmetic compositions.

13. The array of claim 1 wherein aid array comprises four different cosmetic compositions.

14. The array of claim 1 wherein the cosmetic composition(s) that effectively camouflages the imperfections on a consumer's skin comprises an average composition C* value of about 2 to about 25 units greater than an average skin C* value of the user.

15. An array of cosmetic compositions intended to camouflage imperfections on human skin in a targeted manner comprising:
   a. from about two to about ten different shades of cosmetic compositions, wherein each shade of cosmetic composition comprises a metal oxide selected from the group consisting of zinc oxide, iron oxide, titanium oxide and mixtures thereof;
   b. wherein said different shades of cosmetic compositions each have a C* value, wherein the C* value for each of said cosmetic compositions is within the range of from about 15 to about 45;
   c. wherein one or more of the cosmetic compositions from the array will effectively camouflage imperfections on a consumer's skin if said consumer has an average skin C* value between about 5 and about 30;
   d. wherein the cosmetic composition(s) that effectively camouflages the imperfections on a consumer's skin comprises an average composition C* value of about 2 to about 25 units greater than an average skin C* value of the user.

* * * * *